United States Patent [19]

Sun

[11] 4,117,020
[45] Sep. 26, 1978

[54] METHOD OF PRODUCING VALUABLE ALKYLATED AROMATIC HYDROCARBONS FROM TAR

[75] Inventor: Yun Chung Sun, Midland, Mich.

[73] Assignee: The Dow Chemical Company, Midland, Mich.

[21] Appl. No.: 785,982

[22] Filed: Apr. 8, 1977

[51] Int. Cl.² .............................................. C07C 3/62
[52] U.S. Cl. ............................ 260/668 C; 260/672 T
[58] Field of Search ...................... 260/668 C, 672 T

[56] References Cited

U.S. PATENT DOCUMENTS

| 3,410,921 | 11/1968 | Pollitzer | 260/672 T |
|---|---|---|---|
| 3,555,103 | 1/1971 | Strohmeyer | 260/672 T |
| 3,763,259 | 10/1973 | Hervert | 260/672 T |

Primary Examiner—C. Davis

Attorney, Agent, or Firm—G. R. Plotecher

[57] ABSTRACT

Valuable alkylated aromatic hydrocarbons are produced from a tar comprising that fraction of an alkylation reaction product distilling above about 240° C by a method comprising contacting the tar with benzene and/or toluene in the presence of a catalytic amount of a crystalline aluminosilicate molecular sieve catalyst. For example, tar obtained from the alkylation product resulting from alkylating benzene with ethylene in the presence of aluminum chloride, the tar comprising that fraction of the alkylation reaction product distilling above about 240° C, is converted to a reaction product comprising valuable mono- and diethylbenzene by contacting the tar with benzene in the presence of a catalytic amount of a rare earth exchange zeolite Y molecular sieve at a temperature of at least about 240° C and at a pressure of at least about 200 psi.

23 Claims, No Drawings

METHOD OF PRODUCING VALUABLE ALKYLATED AROMATIC HYDROCARBONS FROM TAR

BACKGROUND OF THE INVENTION

1. Field of the Invention

This invention relates to valuable alkylated aromatic hydrocarbons. In one aspect, this invention relates to a method of producing said hydrocarbons from otherwise marginally valuable tar obtained from the reaction product of an alkylation process comprising contacting benzene and/or toluene with a $C_2$-$C_3$ olefin. In another aspect, this invention relates to said method wherein the tar is contacted with benzene and/or toluene in the presence of a crystalline aluminosilicate molecular sieve catalyst.

2. Description of the Prior Art

The reaction product produced by the alkylation of benzene and/or toluene with ethylene and/or propylene (in the presence of an alkylation catalyst and at alkylation parameters) comprises both valuable alkylated aromatics, such as ethylbenzene, ethyltoluene, cumene, etc., and tar. This tar is a problem in as much as it represents lost alkylated aromatic hydrocarbons. The size of this problem, of course, is dependent upon the amount of tar that can be converted to the alkylated aromatic hydrocarbons. The more tar that can be converted, the smaller the size of the problem. Presently, only the tar fraction that distills below about 240° C is considered convertible while the remaining tar fraction is not so considered (and is thus generally burned as fuel, a marginally valuable utility). Accordingly, the aforementioned alkylation processes are generally conducted in such a manner as to minimize this latter tar fraction. This equates with conducting the alkylations at an olefin:aromatic mole ratio of substantially less than 1 which results in a large amount of unreacted aromatic being present in the resulting reaction product. The unreacted aromatic must then be removed from the reaction product and eventually recycled. This all translates into a less efficient and more expensive alkylation process than a similar process wherein the tar fraction above about 240° C is convertible. It is therefore desirable to have a method for converting the tar fraction above about 240° C to valuable alkylated aromatic hydrocarbons.

SUMMARY OF THE INVENTION

According to this invention, valuable alkylated aromatic hydrocarbons of the formula:

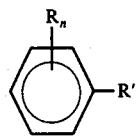

wherein R is

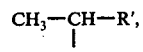

each R' is individually hydrogen or methyl, and n is 1 or 2, are produced from a tar obtained from the reaction product of an alkylation process comprising contacting in the presence of an alkylation catalyst and at alkylation parameters:

(a) benzene, toluene or both; with
(b) ethylene, propylene or both, the tar comprising that fraction of the alkylation reaction product having a distillation temperature of at least about 240° C, by a method comprising contacting at a temperature of at least about 240° C and at a pressure of at least about 200 psi:

(i) the tar; with
(ii) benzene, toluene or both; in the presence of a catalytic amount of
(iii) a crystalline aluminosilicate molecular sieve catalyst. This invention converts otherwise marginally valuable tar to valuable alkylated aromatic hydrocarbons, and thus allows the alkylation processes to be conducted in a more efficient and less expensive manner than heretofore practical.

DETAILED DESCRIPTION OF THE INVENTION

The valuable alkylated aromatic hydrocarbons produced by this invention are of the formula:

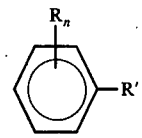

wherein R is

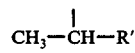

each R' is hydrogen or methyl, and n is 1 or 2. Each R can be either ortho, meta or para to R' as well as to one another (where n is 2). Typically the aromatic hydrocarbons produced are characteristic of the tar from which they are made. For example, the tar obtained from the alkylation process for ethyltoluene typically produces mono- and diethyltoluene when contacted with toluene at conversion conditions. Similarly, the tar obtained from the alkylation processes for ethylbenzene and cumene typically produces mono- and diethylbenzene and mono- and diisopropylbenzene, respectively (when contacted with benzene). R is usually ethyl when R' is methyl.

The tars here used are obtained from the reaction product of an alkylation process comprising contacting in the presence of an alkylation catalyst and at alkylation parameters:

(a) benzene, toluene or both; with
(b) ethylene, propylene or both.

These alkylation reaction products are generally fractionally distilled to recover the various components and the distilland remaining at about 240° C comprises the tars of this invention. In other words, the tars here used comprise that fraction of the alkylation reaction product having a distillation temperature of at least about 240° C, the desired alkylation product and convertible tars having distillation temperatures below about 240° C. Typical alkylation processes include the production of ethylbenzene (ethylene and benzene), ethyltoluene (ethylene and toluene) and cumene (propylene and benzene). The alkylation catalyst and parameters of these processes are not critical and thus any suitable catalyst, e.g., aluminum chloride, zinc chloride and other Friedel-crafts catalysts, and alkylation parameters, e.g., about 80 to about 180° C and about 0 to about 200 psi, can be used.

While the composition of these tars are not known with precision and vary from alkylation process to alkylation process, an illustrative composition is about:

(a) 10 weight percent long chain or cyclic hydrocarbon, such as $C_6$-$C_{20}$ alkyls, cycloalkyls and derivatives of either;

(b) 40 weight percent cyclohexylbenzene and derivatives thereof, such as various cyclohexylalkylbenzenes; and (c) 50 weight percent polyaromatic material, such as 1,4-diphenylbutane, 1,1-diphenyl-ethane, etc. These tars can be further defined as essentially wholly hydrocarbon and substantially free of monoaromatic alkylated material, such as di-, tri- and tetraethylbenzene, di- and tri-isopropylbenzene, and di- and tri-ethyltoluene. These monoaromatic alkylated hydrocarbons are generally considered among the convertible tars and are removed by distillation from the reaction product prior to about 240° C. This invention finds particular utility for tars having a distillation temperature of at least about 270° C, with special utility for tars having a distillation temperature of at least about 290° C.

Crystalline aluminosilicate (zeolite) molecular sieve catalysts are used in the practice of this invention. These catalysts include both naturally occurring and synthetically prepared zeolites and consist basically of a 3-dimensional framework of $SiO_4$ and $AlO_4$ tetrahedrons cross-linked by the sharing of oxygen atoms. The electrovalence of each tetrahedra containing aluminum is balanced by the inclusion in the framework of a cation, such as an alkali or alkaline earth metal ion. These catalysts are known in the art and are further described by Milton, U.S. Pat. Nos. 2,882,244; Breck, 3,130,007; Rabo et al., 3,236,761 and Bowes et al., 3,578,723, all incorporated herein by reference.

Preferred molecular sieve catalysts are of the zeolite Y type and have a pore size of at least about 6 angstroms, and preferably of at least about 8 angstroms. These Y catalysts are of the formula:

$$0.9 \pm 0.2\ Na_2O:Al_2O_3:wSiO_2:xH_2O$$

wherein $w$ is 4–6 and $x$ is 0–9. More preferred Y catalysts comprise about 20 weight percent of an acid washed inorganic oxide binder and comprise by weight about:

(a) 65 percent $SiO_2$;
(b) 20 to about 34 percent $Al_2O_3$;
(c) 0.15 to about 2 percent $Na_2O$; and
(d) 0 to about 12 percent $RE_2O_3$, wherein RE is a rare earth metal having an atomic number between 57 and 71, inclusive.

A rare earth exchange zeolite Y molecular sieve especially preferred is SK-500, a Linde molecular sieve manufactured by the Materials Systems Division of Union Carbide Corporation. This catalyst comprises about:

(a) 65 percent $SiO_2$;
(b) 22.7 percent $Al_2O_3$;
(c) 1.6 percent $Na_2O$; and
(d) 10.7 percent $RE_2O_3$.

A catalytic amount of molecular sieve catalyst is required for the practice of this invention. Typically, the molecular sieve catalyst is present at a minimum sieve:tar weight ratio of about 0.01:1 and preferably of about 0.1:1. A maximum sieve:tar weight ratio here used is typically about 2:1 and preferably about 1:1. These maximum sieve:tar weight ratios are only typical with the actual maximums determined by practical considerations, such as convenience and economy.

This invention also requires that the tar be contacted with an aromatic, typically benzene, toluene or both. The aromatic employed is a matter of choice but generally benzene is contacted with tars generated from an ethylbenzene or cumene process while toluene is contacted with tars generated from a ethyltoluene process. Any suitable amount of benzene and/or toluene can be contacted with the tars. Illustrative amounts include benzene with ethylbenzene tar at a minimum benzene:tar weight ratio of about 0.01:1, and preferably about 0.5:1 and a maximum weight ratio of about 5:1 and preferably about 2:1. Like weight ratios for benzene and cumene tar and toluene and ethyltoluene tar are used.

While this invention can be practiced in either the liquid or gaseous state, the temperature and pressure parameters here used are generally sufficient to maintain the process reagents (excepting the catalyst) in the liquid state. The tar and the benzene and/or toluene are contacted at a temperature of at least about 240° C and at a pressure of at least about 200 psi. A minimum temperature of about 270° C is preferred with a maximum temperature of about 400° C, and preferably of about 350° C. A pressure of at least about 300 psi is preferred, with a maximum pressure of about 900 psi, and preferably about 600 psi.

Hydrogen addition to the reaction mixture of tar, benzene and/or toluene, and catalyst is generally neither beneficial nor detrimental as regards tar conversion to valuable aromatic hydrocarbons. As such, hydrogen is generally not added to the reaction mixture.

This invention can also be practiced either on a batch or a continuous basis. Economy and convenience prefers the latter.

The following examples are illustrative of certain specific embodiments of this invention. Unless otherwise noted, all parts and percentages are by weight.

SPECIFIC EMBODIMENTS

EXAMPLE 1

Ethylbenzene tar (130 gms) obtained from the reaction product of the alkylation process comprising contacting benzene and ethylene in the presence of aluminum chloride and at a temperature of about 110° C and a pressure of about 15 psi (the tar comprising that fraction of the alkylation reaction product distilling between a temperature range of about 270°–350° C) was added to a batch reactor containing benzene (300 gms) and SK-500 (50 gms), a Linde molecular sieve catalyst comprising about 65 percent $SiO_2$, about 22.7 percent $Al_2O_3$, about 1.6 percent $Na_2O$, and about 10.7 percent $RE_2O_3$, manufactured by the Materials Systems Division of Union Carbide Corporation. The batch reactor was then heated to about 280° C and 500 psi and maintained thereat for about two hours. The resulting reaction product was then distilled and analyzed by vapor phase chromatography. Analysis showed a substantial conversion of the ethylbenzene tar and a distillate composite (385 g) comprising:

| | |
|---|---|
| Benzene | 70% |
| toluene | 3.3% |

| | |
|---|---|
| Ethylbenzene | 17.5% |
| Diethylbenzene and others | 9.2% |

Residue after distillation comprised about 45 gms.

EXAMPLE 2

The residue (45 gms) from Example 1 was added to a batch reactor containing benzene (160 gms) and SK-500 catalyst (50 gms). The reactor was then heated to about 280° C at 500 psi and maintained thereat for about 2 hours. Subsequent distillation and vapor phase chromatography showed further conversion of the original ethylbenzene tar with a distillate composition (183 g) of:

| | |
|---|---|
| Benzene | 90.8% |
| Toluene | 2.1% |
| Ethylbenzene | 3% |
| Diethylbenzene and others | 3.8% |

A second residue (22 gms) remained after this distillation.

EXAMPLE 3

Ethyltoluene tar (130 gms) obtained from the reaction product of the alkylation process comprising contacting toluene and ethylene in the presence of AlCl$_3$ at a temperature of about 150° C and at a pressure of about 15 psi (the tar comprising that fraction of the alkylation reaction product distilling between the temperature range of about 240°–350° C) was added to a batch reactor containing toluene (270 gms) and SK-500 molecular sieve catalyst (50 gms). The reactor was heated to about 320° C and 500 psi and maintained thereat for about 2 hours. Subsequent distillation (up to about 190° C) and vapor phase chromatography revealed a conversion of about 64 percent of tar to valuable alkylated aromatic hydrocarbons. The reaction product contained about 22 percent ethyltoluene ($\approx$88 g).

EXAMPLE 4

The procedure of Example 3 was repeated except isopropylbenzene tar (250°–350° C) was substituted for ethyltoluene tar and benzene was substituted for toluene. Analysis of the reaction product revealed about 67 percent conversion of the tar to valuable alkylated aromatic hydrocarbons. The reaction product contained about 27 percent isopropylbenzene ($\approx$108 g).

Although this invention has been described in considerable detail by the preceding examples, it is to be understood that such detail is for purposes of illustration only and are not to be construed as limitations upon the invention. Many variations may be had upon the preceding examples without departing from the spirit and scope of the appended claims.

What is claimed is:

1. A method of producing valuable alkylated aromatic hydrocarbons of the formula:

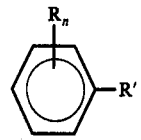

wherein R is

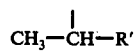

each R' is individually hydrogen or methyl, and $n$ is 1 or 2, from a tar obtained from the reaction product of an alkylation process comprising contacting in the presence of an alkylation catalyst and at alkylation parameters:

(a) benzene, toluene or both; with
(b) ethylene, propylene or both, the tar being substantially free of monoaromatic alkylated material and comprising that fraction of the alkylation reaction product having a distillation temperature of at least about 240° C, the method comprising contacting at a temperature of at least about 240° C and at a pressure of at least about 200 psi:

(i) the tar, with
(ii) benzene, toluene or both; in the presence of a catalytic amount of
(iii) a crystalline aluminosilicate molecular sieve catalyst.

2. The method of claim 1 wherein the molecular sieve catalyst is a zeolite Y having a pore size of at least about 6 angstroms.

3. The method of claim 2 wherein the molecular sieve catalyst comprises about 20 weight percent of an acid washed inorganic oxide binder.

4. The method of claim 3 wherein the molecular sieve catalyst comprises, by weight, about:
(a) 65 percent SiO$_2$;
(b) 20 to about 34 percent Al$_2$O$_3$;
(c) 0.15 to about 2 percent Na$_2$O; and
(d) 0 to about 12 percent RE$_2$O$_3$, wherein RE is a rare earth metal having an atomic number between 57 and 71, inclusive.

5. The method of claim 4 wherein the molecular sieve catalyst comprises, by weight, about:
(a) 65 percent SiO$_2$;
(b) 22.7 percent Al$_2$O$_3$;
(c) 1.6 percent Na$_2$O; and
(d) 10.7 percent RE$_2$O$_3$.

6. The method of claim 5 wherein the tar is obtained from the reaction product of an alkylation process comprising contacting benzene and ethylene.

7. The method of claim 6 wherein the tar is contacted with benzene.

8. The method of claim 7 wherein the tar and benzene are contacted at a temperature between about 270° and 350° C, inclusive, and at a pressure between about 300 and about 600 psi, inclusive.

9. The method of claim 8 wherein the tar and benzene are present at a benzene:tar weight ratio between about 0.5:1 and about 2:1, inclusive.

10. The method of claim 9 wherein the tar and molecular sieve are present at a sieve:tar weight ratio between about 0.1:1 and about 1:1, inclusive.

11. The method of claim 5 wherein the tar is obtained from the reaction product of an alkylation process comprising contacting toluene and ethylene.

12. The method of claim 11 wherein the tar is contacted with toluene.

13. The method of claim 12 wherein the tar and toluene are contacted at a temperature between about 270° and about 350° C, inclusive, and at a pressure between about 300 and about 600 psi, inclusive.

14. The method of claim 13 wherein the tar and toluene are present at a toluene:tar weight ratio between about 0.5:1 and about 2:1, inclusive.

15. The method of claim 14 wherein the tar and molecular sieve are present at a sieve:tar weight ratio between about 0.1:1 and about 1:1, inclusive.

16. The method of claim 5 wherein the tar is obtained from the reaction product of an alkylation process comprising contacting benzene and propylene.

17. The method of claim 16 wherein the tar is contacted with benzene.

18. The method of claim 17 wherein the tar and benzene are contacted at a temperature between about 270° and about 350° C, inclusive, and at a pressure between about 300 and about 600 psi, inclusive.

19. The method of claim 18 wherein the tar and benzene are present at a benzene:tar weight ratio between about 0.5:1 and about 2:1, inclusive.

20. The method of claim 19 wherein the tar and molecular sieve are present at a sieve:tar weight ratio between about 0.1:1 and about 1:1, inclusive.

21. The method of claim 1 wherein the tar comprises that fraction of the alkylation reaction product having a distillation temperature of at least about 270° C.

22. The method of claim 1 wherein the tar comprises that fraction of the alkylation reaction product having a distillation temperature of at least about 290° C.

23. The method of claim 1 wherein the tar comprises about:
   (a) 10 weight percent long-chain or cyclic hydrocarbon;
   (b) 40 weight percent cyclohexylbenzene and derivatives thereof; and
   (c) 50 weight percent polyaromatic material.

* * * * *